United States Patent
Farah et al.

(10) Patent No.: US 6,375,987 B1
(45) Date of Patent: Apr. 23, 2002

(54) PROCESS FOR THE MANUFACTURE OF PHARMACEUTICAL COMPOSITION WITH MODIFIED RELEASE OF ACTIVE PRINCIPLE COMPRISING THE MATRIX

(75) Inventors: Nabil Farah, Lyons; Philippe Bärthelemy, Moins; Joseph Joachim, Marseilles, all of (FR)

(73) Assignee: Gattefossé, S.A., Saint-Priest Cedex (FR)

(*) Notice: Subject to any disclaimer, the term of this patent is extended or adjusted under 35 U.S.C. 154(b) by 0 days.

(21) Appl. No.: 09/718,613

(22) Filed: Nov. 22, 2000

Related U.S. Application Data

(62) Division of application No. 09/269,468, filed as application No. PCT/FR97/01710 on Sep. 29, 1997, now Pat. No. 6,194,005.

(30) Foreign Application Priority Data

Oct. 1, 1996 (FR) .............................. 96 12516

(51) Int. Cl.⁷ .............................. A61K 9/14; A61K 9/16
(52) U.S. Cl. ........................................ 424/489; 424/490
(58) Field of Search .................................. 424/489, 490

(56) References Cited

U.S. PATENT DOCUMENTS 3,700,013 A * 10/1972 Coffey et al.
4,572,833 A * 2/1986 Pedersen et al.

* cited by examiner

Primary Examiner—Thurman K. Page
Assistant Examiner—Amy E Pulliam
(74) Attorney, Agent, or Firm—Norris, McLaughlin & Marcus

(57) ABSTRACT

The invention relates to a process for the manufacture of a pharmaceutical composition with modified release of active principle comprising at least one active principle, a lipid matrix agent composed of ester of alcohol with at least one fatty acid and at least one adjuvant.

This process is characterized in that:

a powder composed of at least one component selected in the group comprising the active principle and the adjuvant, is mixed, while heating and fluidizing, in order to obtain individual grains;

the said lipid matrix agent is liquefied separately under warm conditions;

the said powder is then coated under warm conditions by spraying the said lipid matrix agent over the individual grains;

finally, the temperature of the combined product is lowered in order to allow the lipid matrix agent to solidify.

4 Claims, 7 Drawing Sheets

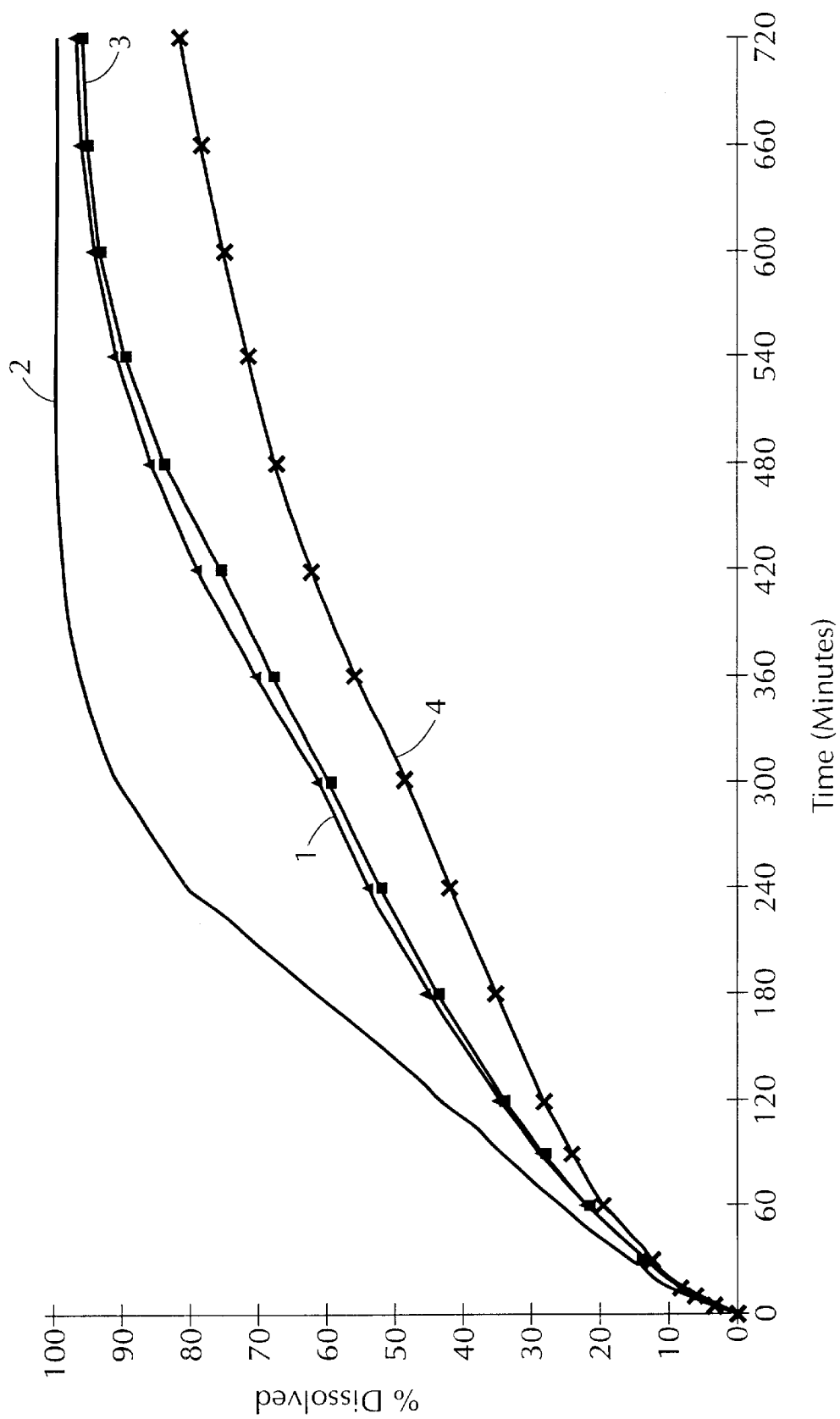

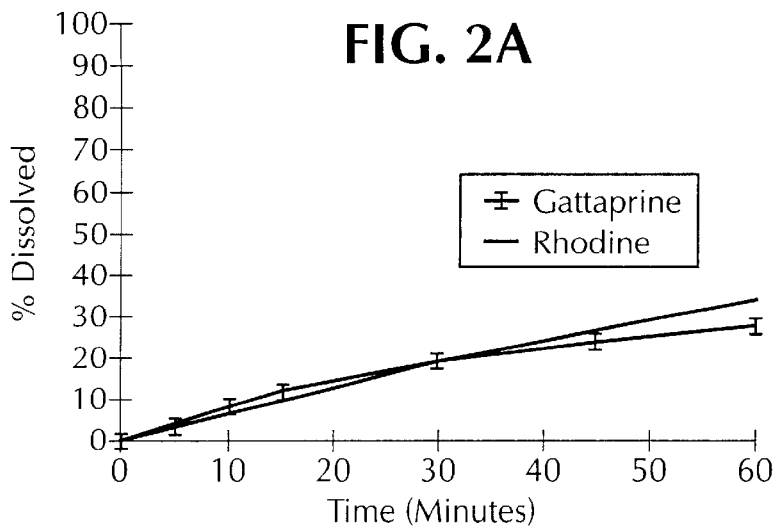
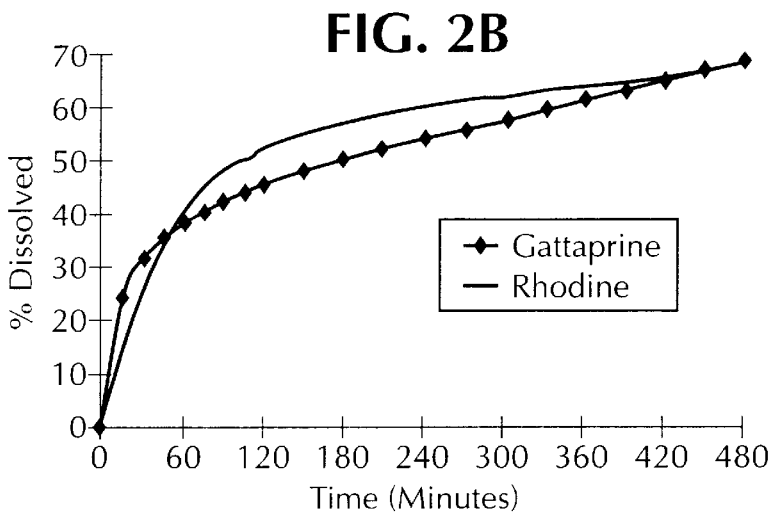
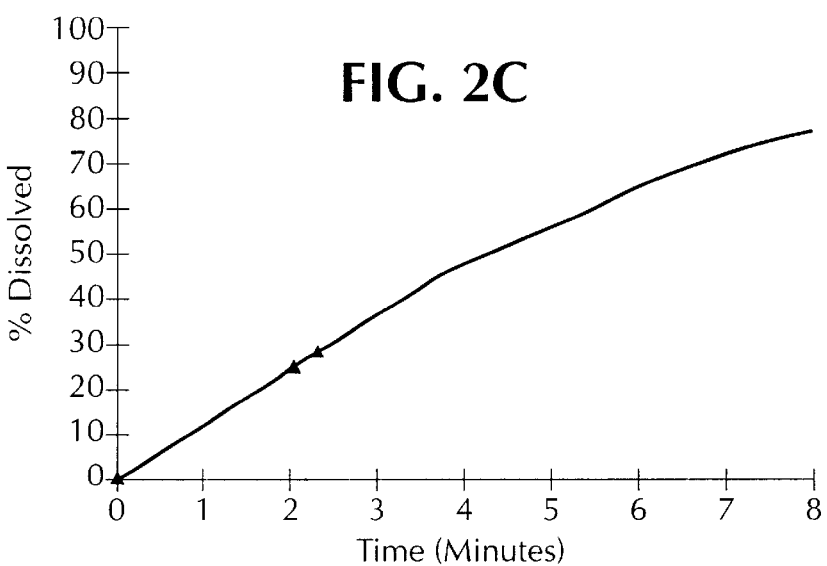

PROCESS FOR THE MANUFACTURE OF PHARMACEUTICAL COMPOSITION WITH MODIFIED RELEASE OF ACTIVE PRINCIPLE COMPRISING THE MATRIX

CROSS-REFERENCE TO RELATED APPLICATIONS

This is a divisional application of Ser. No. 09/269,468 filed Mar. 23, 1999, now U.S. Pat. No. 6,194,005, which in turn was a national phase filing of International Application No. PCT/FR97/01710 filed Sep. 29, 1997.

The invention relates to a process for the manufacture of a pharmaceutical composition with modified release of active principle comprising a matrix.

THE PRIOR ART

"Pharmaceutical composition with modified release of active principle" denotes the pharmaceutical compositions with accelerated, sustained and delayed release of active principle.

Various types of pharmaceutical compositions with modified release of active principle exist. Compositions comprising, on the one hand, uncoated granules constituting the dose of immediately available active principle and, on the other hand, coated granules providing for the modified release of active principle are particularly used.

Compositions comprising a matrix effect are also used.

The invention more particularly relates to the process for manufacturing the latter.

In this type of composition, the active principle is dispersed or coated in a solid system, known as a matrix. The release of the active principle from the matrix is achieved by contact of biological fluids with the said matrix. More specifically, biological fluids migrate through the matrix and dissolve the active principles and the latter are released by diffusion through the matrix which, simultaneously, modulates the release flow.

Hydrophilic matrices and hydrophobic matrices are distinguished.

In compositions comprising a hydrophilic matrix, the matrix is composed of an insoluble hydrophilic polymer, the concentration of which is between 25% and more than 50% of the weight of the composition, therefore high. This polymer is chosen from cellulose esters, carboxyvinyl esters, or acrylic or methacrylic esters. On contact with biological fluids, the matrix becomes hydrated and swells, forming a very dense network of polymers, through which polymers the soluble active principles diffuse. Furthermore, lipids, in particular glyceryl esters, as illustrated, for example, in the document FR-B-2,573,307, can be added in order to modulate the matrix swelling. In addition, these compositions include numerous adjuvants, often expensive adjuvants, at high concentrations, which greatly increases the cost of the composition.

These compositions are obtained by granulation and then compression of the mixture formed of the polymer, active principles and various adjuvants. These techniques often involve the use of organic solvents, which it is subsequently essential to recover in order to prevent them from dispersing into the atmosphere. In addition, traces of toxic solvents can remain in the final product, which traces necessarily have to be quantified.

In other words, the preparation of these compositions results in a high production cost, due to the cost of the various constituents of the composition, to their high proportions and to the technical constraints to be overcome.

In the compositions comprising a hydrophobic matrix, the matrix is composed of a lipid matrix agent of natural origin, for example beeswaxes, which is highly innocuous However, its composition varies from one batch to another and its stability over time is not very satisfactory.

As above, these compositions are generally obtained by granulation, by a wet or solvent route, and then compression, involving high proportions of each of the constituents.

The aim of the invention is thus to provide a novel process for the manufacture of a pharmaceutical composition with modified release of active principle by having the object of significantly decreasing the number and the proportions of each of the constituents as well as the number of operations, thus making it possible to obtain a formulation which is simple to employ and of low and reproducible cost.

DETAILED DESCRIPTION OF THE INVENTION

To overcome this combination of problems, the invention provides a process for the manufacture of a pharmaceutical composition with modified release of active principle comprising at least one active principle, a lipid matrix agent composed of an ester of at least one fatty acid and of alcohol, and at least one adjuvant.

This process is characterized in that:
  a powder composed of at least one component selected from the group comprising the active principle and the adjuvant is mixed, while heating and fluidizing, in order to obtain individual grains,
  the said lipid matrix agent is liquefied separately under warm conditions,
  the said powder is then coated under warm conditions by spraying the said lipid matrix agent over the individual grains, and, finally, the temperature of the combined product is lowered in order to allow the lipid matrix agent to solidify.

In other words, the invention lies in the employment of a specific process which makes it possible to decrease the number of adjuvants necessary for the preparation of the composition and thus to result in an extremely simple and low-cost formula.

In addition, the process of the invention does not require an evaporation phase or a drying phase, since it does not require a wet-route or solvent-route granulation step, thus making it possible to be freed from any risk due to the presence of toxic residues in the final product. Furthermore, it is no longer necessary to carry out the quantitative determination of the traces of solvents, an analysis which is very expensive.

According to the process of the invention, the praying conditions and thus the coating characteristics can be modified, in order to vary the release profile of the active principle, by varying several parameters, the adjustment characteristics of which remain simple.

Thus, the spraying air pressure can be increased in order to promote the formation of a homogeneous film of lipid matrix agent around the grains.

Advantageously, the rate of spraying of the lipid matrix agent can simultaneously be decreased.

In this case, an active principle release profile, that is to say a percentage of dissolution as a function of the time, is obtained which is very low, corresponding to a slow release of the active principle.

Conversely, the spraying air pressure can be decreased in order to promote the agglomeration of the grains with one another.

Advantageously, the rate of spraying of the lipid matrix agent can simultaneously be increased.

In this case, a release profile of the grains obtained is obtained which is very high, corresponding to a rapid release of the active principle.

In practice and according to the mass of powder employed, the value of the rate of spraying of the lipid matrix agent is from two to four times higher when it is desired to promote the agglomeration of the grains with one another than when it is desired to promote the formation of a homogeneous film around the grains.

On the other hand, the value of the spraying air pressure is from one to two times lower when it is desired to promote the agglomeration of the grains with one another than when it is desired to promote the formation of a homogeneous film around the grains.

According to the process of the invention, it is possible, after having determined a given active principle release profile, to vary the values of spraying air pressure and of spraying rate throughout the coating stage, making it possible to promote the formation of a homogeneous film around the grains or to promote the agglomeration of the grains.

Once the sequence of the duration of the spraying air pressure and of the spraying rate has been determined, the coating operation can be carried out continuously and automatically.

According to another characteristic of the invention, the temperature of the mixture of liquefied matrix agent and of spraying air must be greater by 35° C. to 60° C. than the melting temperature of the lipid matrix agent.

Likewise, the temperature of the fluidization air and that of the powder must be equal to the melting temperature of the lipid matrix agent, plus or minus 10° C.

Furthermore, in order to obtain a mixture of individual grains, an air-operated fluidized bed device or a turbine device is used.

Furthermore, the lipid matrix agent can be sprayed by the air spray technique, that is to say liquid spraying under pressure in the presence of compressed air.

According to a first embodiment, use is made of a powder comprising the active principle and the adjuvant. In other words, after mixing and fluidizing the combined constituents of the powder, the lipid matrix agent is sprayed over the individual grains obtained.

When it is desired to package the product obtained in the form of a sachet or hard gelatin capsule, the spraying air pressure and the rate of spraying of the lipid matrix agent are adjusted to a value which makes it possible to promote the formation of a homogeneous film of lipid matrix agent around the grains.

When it is desired to obtain tablets, the coated grains are subjected to a compression stage.

In an entirely surprising way, it is found that, in the case where the individual grains are coated while promoting the formation of a homogenous film around the said grains, whereas they exhibit a very low release profile before compression, they exhibit, in contrast, a high release profile after compression.

Conversely, and in just as surprising a way, in the case where agglomeration of the individual grains is promoted, whereas the said grains exhibit a high release profile before compression, they exhibit, in contrast, a low release profile after compression.

As already said, it thus appears highly advantageous to vary the spraying conditions throughout the coating operation in order to more or less promote the release of the active principle.

According to another embodiment of the invention, a powder composed exclusively of the active principle is used.

According to this technique, the coated grains of active principle are mixed under cold conditions with uncoated adjuvants.

Likewise, a powder composed exclusively of adjuvant(s) can be used.

In this case, the coated adjuvant grains are mixed with the uncoated active principle.

As above, in order to obtain tablets, the mixture obtained is subjected to a compression stage.

The mixture obtained can be directly packaged in the form of sachets or hard gelatin capsules.

In order to avoid adhesion of the coated grains obtained, whether in the case where all the grains are treated or whether in the case where only a portion of the grains is treated, a stage of lubrication of the grains is inserted between the coating stage and the stage of putting into a pharmaceutical form.

Furthermore, in order to obtain greater stability of the pharmaceutical composition, that is to say in order to minimize modifications relating to the release of the active principle or principles over time, the granules or tablets obtained can be subjected to a maturing stage in an oven, for at least 8 hours, at a temperature of between 45 and 60° C., advantageously 55° C.

In order to solve the problem of obtaining a composition in which the proportions of constituents are low, use is made of an amount of matrix agent representing, by weight, from 1 to 15% of the final composition, advantageously from 2 to 5%.

Success is not achieved in obtaining an even coating for a value of lipid matrix agent of less than 1%.

The process becomes much less advantageous economically for a value greater than 15%.

These proportions are thus very low with respect to those used in the prior art, in particular in the abovementioned document FR-B-2,573,307, in which the proportions disclosed are much greater than 15% by weight of the final composition, generally 30%.

According to a first embodiment of the invention, use is made, as lipid matrix agent, of an ester of behenic acid and of alcohol.

The alcohol is advantageously chosen from the group comprising glycerol, polyglycerol, propylene glycol, propylene glycol in combination with ethylene oxide and polyethylene glycol.

These matrix agents exhibit the advantage of having a melting point of greater than 50° C., which prevents them from disintegrating at the compression temperature. Furthermore, this melting point is greater than the internal temperature of the human body (37° C.), which allows the lipid agent to have a more pronounced matrix behaviour.

In addition, the spraying of an ester of fatty acid and of alcohol as lipid matrix agent makes it possible, in addition to the fact of accelerating or of slowing down the release of the active principle, furthermore to mask the taste of the starting material. This is truly advantageous insofar as none of the current masking techniques makes it possible to mask the taste of the starting materials without excessively slowing down the release of the active principle.

Use is advantageously made of the ester of behenic acid and of glycerol exhibiting a melting point of between 69 and 74° C. and therefore much greater than 50° C. This ester results from the direct esterification of behenic acid with glycerol, to result in a mixture of glyceryl mono-, di- and tribehenate.

According to another embodiment, the lipid matrix agent is an ester of palmitic/stearic acid and of alcohol.

According to another characteristic of the invention, the adjuvant is chosen from hydrophobic diluting agents, hydrophilic diluting agents, binding agents or lubricating agents, alone or as a mixture.

In an advantageous embodiment, the hydrophobic diluting agent is dicalcium phosphate and the hydrophilic diluting agent is lactose.

Dicalcium phosphate exhibits the advantage of being very low in cost, which contributes to reducing the final cost of the composition.

Furthermore, the use of lactose as hydrophilic diluting agent makes it possible to adjust the hydrophilic/lipophilic balance necessary for the release of active principle.

In order to promote the compressibility of the grains during the manufacture of tablets, use is made of polyvinylpyrrolidone as binding agent, which makes it possible to decrease the compressive forces of the pharmaceutical composition.

In order to avoid the adhesion of the powder to the walls of the machine during the compressing operation, the pharmaceutical composition comprises a lubricating agent chosen within the group comprising magnesium stearate and silicone-treated talc, alone or in combination.

The silicone-treated talc is advantageously composed of 80% talc and 20% silicone oil.

The invention also relates to the composition obtained by the process described above.

Nevertheless, this modified-release pharma-eutical composition can be obtained by other processes and in particular that of wet granulation, in which use is made of water as granulation solvent.

A wet granulation of the products constituting the powder is thus carried out in a known way in order to succeed in obtaining granules, which are either introduced into capsules or agglomerated by pressing in order to obtain tablets.

The advantages which result from the invention will emerge more clearly from the following implementational examples.

FIG. 1 is a representation as a function of the time of the dissolution profile of batches of theophylline tablets which are prepared by the process of the invention.

FIG. 2 is a representation as a function of the time of the dissolution profile of a batch of coated granules (2A,2B) and of tablets (2C) of acetylsalicylic acid which is manufactured according to the process of the invention.

EXAMPLE 1

Figure 3A:
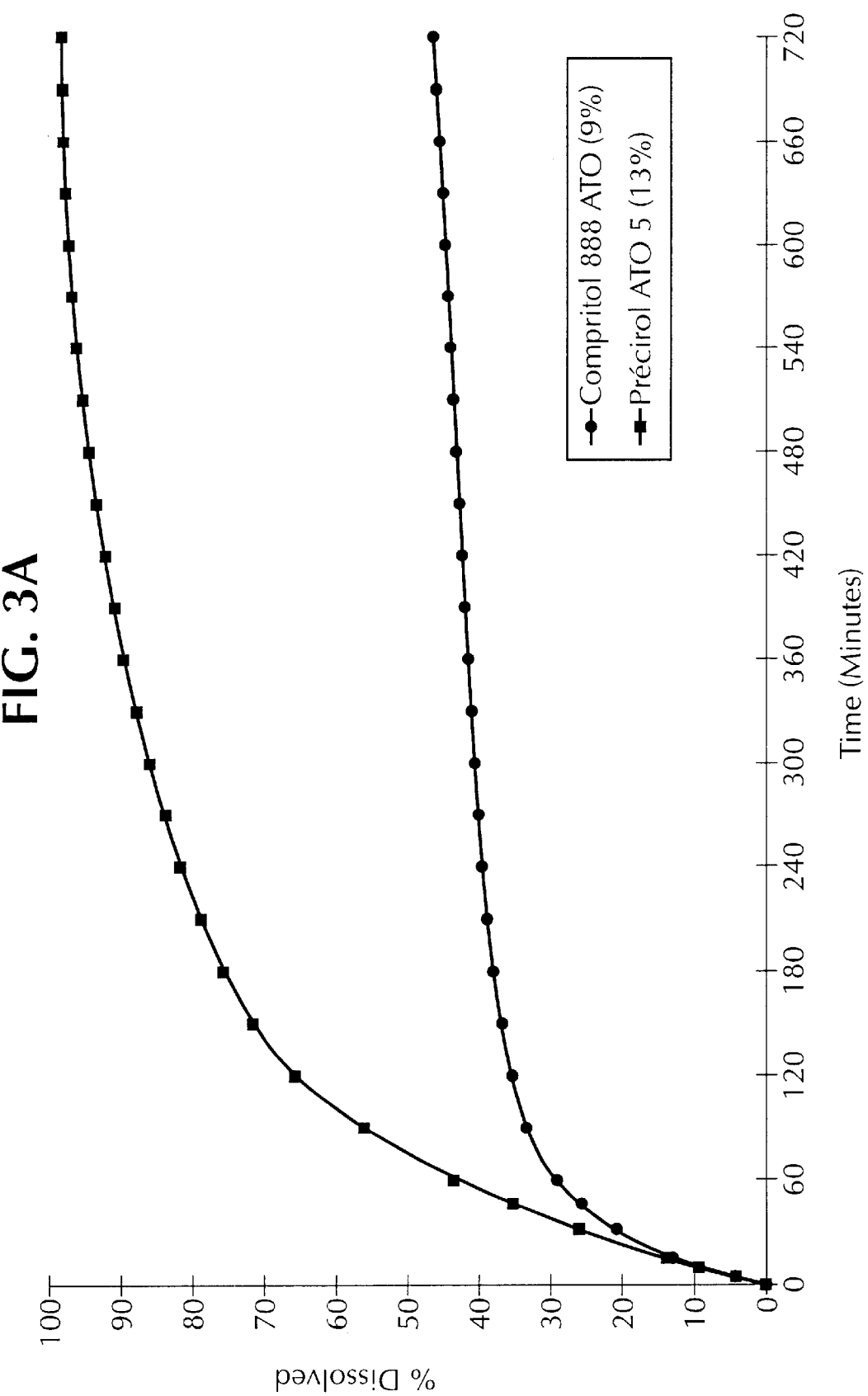
FIG. 3 is a representation as a function of the time of the dissolution profile of a batch of coated granules (3A) and of tablets (3B) of paracetamol which are manufactured according to the process of the invention.

A mixture of 3 kg of powder is prepared comprising:

| | |
|---|---|
| active principle: theophylline | 1920 g |
| hydrophobic diluting agent: | |
| dicalcium phosphate dihydrate | 90 g |
| binding agent: polyvinylpyrrolidone | 90 g |

Four batches of granules are prepared by the process of the invention comprising the following stages:
the mixture of powder obtained is sieved;
the said powder is mixed, heating while by means of an air-operated fluidized bed, in order to obtain individual grains;
the lipid matrix agent (glyceryl behenate, sold by the Applicant Company under the trade name Compritol® 880 ATO) is liquefied separately at 120° C. Celsius;
the lipid matrix agent is sprayed over the heated powder mixture,
and, finally, the temperature is lowered in order to allow the lipid matrix agent to solidify.

These stages are carried out while varying various parameters, either in order to promote the formation of a homogeneous film around the grains or in order to promote the agglomeration of the grains, in accordance with the following table:

| Parameters | Batch 1 | Batch 2 | Batch 3 | Batch 4 |
|---|---|---|---|---|
| % by weight of lipid matrix agent (Compritol ® 888 ATO) | 5 | 4 | 4 | 5 |
| Fluidization air flow rate (m³/h) | 80 | 110 | 80 | 80 |
| Agglomeration | | | | |
| Atomization air pressure (bar) | 2 | | 1.5 | 1.5 |
| Temperature of the powder bed (° C.) | 70 | | 70 | 74 |
| Spraying rate for Compritol ® (g/min) | 42 | | 40 | 40 |
| Coating | | | | |
| Atomization air pressure (bar) | 2.5 | 3.5 | 2 | 2 |
| Temperature of the powder bed (° C.) | 70 | 66 | 71 | 70 |
| Spraying rate for Compritol ® (g/min) | 41 | 20 | 40 | 40 |

The granules thus obtained are mixed in a mixer for 10 minutes with a lubricant comprising 1% of magnesium stearate and 2% of silicone-treated talc with respect to the weight of the preparation.

In order to obtain the silicone-treated talc, a level of 20% by weight of silicone oil (dimethicone fluid 100 CST from Dow Corning) is incorporated in 80% of talc by weight.

The dissolution profile of batches of tablets obtained, after a stage of compression of the granules, according to the parameters of the preceding table, comprising 100 milligrams of theophylline, has been represented in FIG. 1.

Curve 1 corresponds to Batch 1.
Curve 2 corresponds to Batch 2.
Curve 3 corresponds to Batch 3.
Curve 4 corresponds to Batch 4.

These curves show that the release of active principle from the matrix is a function of the parameters of spraying air pressure and of spraying rate of the lipid matrix agent.

As regards Batch 1, first the agglomeration of the grains is promoted by maintaining the spraying air pressure at 2 bar and this pressure is increased to 2.5 bar in order to promote the formation of a homogeneous film around the grains.

In this case, after compression, a relatively high release profile is obtained.

As regards Batch 2, the formation of a homogeneous film of lipid matrix agent around the grains is more favoured by setting the spraying air pressure at 3.5 bar and by decreasing the spraying rate.

In an entirely surprising way, after compression, a very high release profile is obtained.

As regards Batches 3 and 4, the spraying air pressures are adjusted to values which make it possible to promote agglomeration of the grains (1.5 bar) and then the formation of the homogeneous film of lipid matrix agent around the grains (2 bar) continuously during the spraying stage.

It is very surprisingly observed that, after compression, very low release profiles are obtained.

Furthermore, it is found that very good release profiles are obtained, this being achieved with very low proportions of matrix agent of the order of 4 to 5% by weight of the final composition.

EXAMPLE 2

The process of the invention is carried out, which process consists in that:

a powder composed of 100 grams of acetyl-salicylic acid is mixed, while heating, by means of an air-operated fluidized bed device, in order to obtain individual grains, 3 grams of lipid matrix agent (Compritol®) are subsequently liquefied separately;

the acetylsalicylic acid powder is then coated by spraying the lipid matrix agent over the individual grains;

and, finally, the temperature is lowered in order to allow the lipid matrix agent to solidify.

Coated granules of acetylsalicylic acid are obtained, which granules are sold by the Applicant under the trade name Gattaprine.

The profile of the dissolution in acidic medium of Gattaprine, with respect to acetylsalicylic tablets coated with ethylcellulose which are sold by Rhone-Poulenc under the trade name "Rhodine NC RP", has been represented in FIG. 2 (FIG. 2A).

The same dissolution test was carried out in basic medium in FIG. 2B.

The dissolution tests are carried out according to the method of the pharmacopoeia (USP XXIII).

The coated granules of acetylsalicylic acid obtained are subsequently mixed with a powder consisting of:

11.25 grams of microcrystalline cellulose, 2.25 grams of talc, 1.25 grams of magnesium stearate.

The mixture obtained is subsequently subjected to a compression stage in order to obtain microencapsulated tablets of acetylsalicylic acid.

The dissolution profile of batches of tablets of acetylsalicylic acid which is prepared according to the invention has been represented in FIG. 2C.

The tablets thus prepared exhibit the advantage of being devoid of any organic solvent and the final product therefore does not exhibit any toxic risk. In addition, the process makes it possible to obtain products exhibiting good stability. This is because the lipid matrix substance makes it possible to protect the active principle from any phenomenon of moisture during its storage, so that the hydrolysis of the active principle is greatly reduced.

EXAMPLE 3

In this example, the release profile of coated paracetamol is compared for two different lipid matrix agents.

Example 2 is repeated, acetylsalicylic acid being replaced by paracetamol. In addition, 9 g of Compritol® are used.

The various operations are repeated, Compritol® being replaced by an ester of palmitic/stearic acid and of alcohol sold by the Applicant under the trade name "Précirol ATO 5®". Thus, 100 g of paracetamol are coated with 13 g of Précirol ATO 5.

The release profile of a batch of paracetamol, thus coated, has been represented in FIG. 3.

It is found that the release profile of the paracetamol is higher when Précirol ATO 5® is used than when Compritol® is used.

As in Example 2, the coated granules of paracetamol obtained are subsequently mixed with a powder consisting, in the same proportions, of microcrystalline cellulose, of talc and of magnesium stearate and then the mixture obtained is subjected to a compression stage.

Figure 3B:
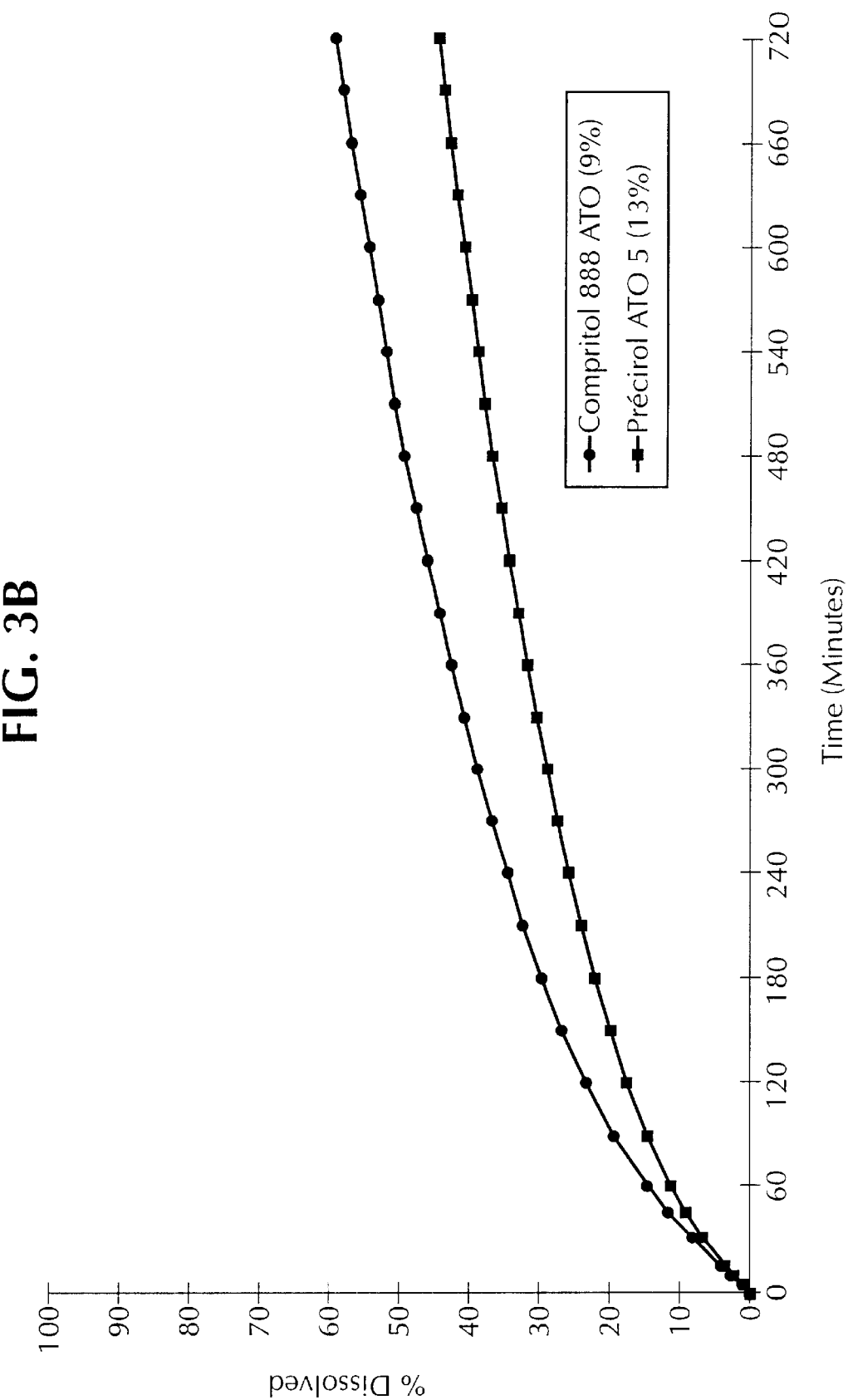

The release profile of the tablets thus obtained has been represented in FIG. 3B.

It is observed that, surprisingly, the release profile of the dissolved paracetamol is higher when Compritol® is used than when Précirol ATO® is used.

EXAMPLE 4 to 6

In the examples which follow, pharmaceutical compositions with release of active principle are prepared by a wet granulation process.

EXAMPLE 4

One hundred grams (100 g) of granules are prepared comprising, as a mixture:

| | |
|---|---|
| active principle: ibuprofen | 60 g |
| hydrophobic diluting agent: dicalcium phosphate dihydrate | 13 g |
| hydrophilic diluting agent: lactose | 15 g |
| lipid matrix agent: qlyceryl behenate, sold by the Applicant under the registered trade name Compritol ® 888 ATO | 12 g |

The granules are prepared by a wet granulation process in a mixer/granulator comprising the following stages:

prior sieving of each of the constituents, mixing the active principle and the adjuvants for five minutes, gradual addition of 60 ml of distilled water and then mixing for 130 seconds, predrying the granules in an oven at a temperature of 45° C. for 20 minutes, screening carried out on a screening device (1.25 millimetre screen), drying in an oven at a temperature of 45° C. for 12 hours.

The granules thus obtained are subsequently mixed in a mixer with a lubricant, the composition of which is identical to that in Example 1.

In order to obtain tablets, the granules obtained are compressed with an alternating compression machine well known for this application.

Figure 4:
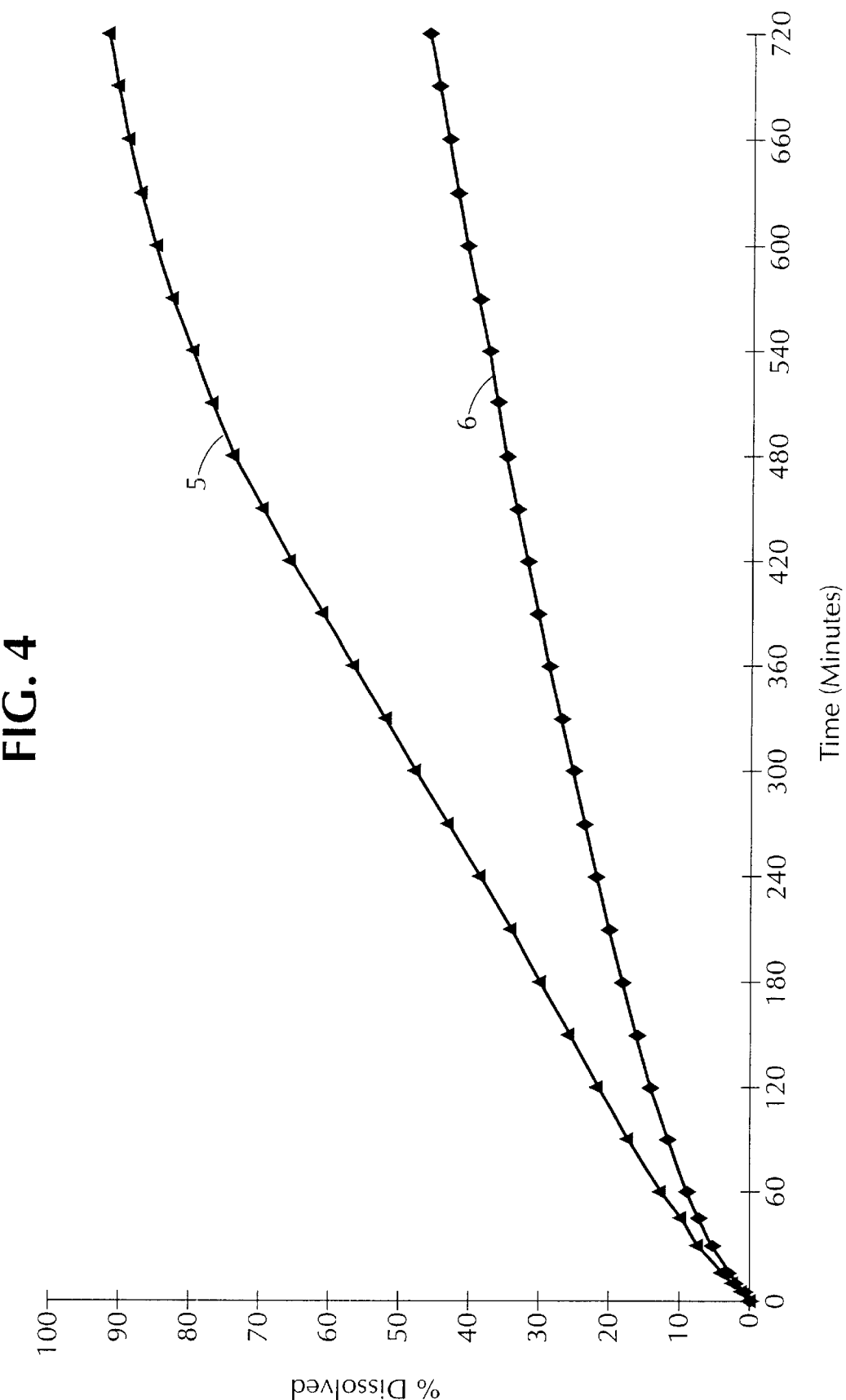
FIG. 4 is a representation as a function of the time of the dissolution profile of a pilot batch of ibuprofen tablets which is prepared by wet granulation.

FIG. 4 is a representation of the dissolution profile of a pilot batch, prepared according to the invention, of tablets comprising 300 mg of ibuprofen at pH 6.8 (in vitro).

The level of lipid matrix agent was determined in order to obtain a release profile of 90% of active principle over 12 hours.

Curve 5 corresponds to a batch which has not been subjected to a maturing operation.

Curve 6 corresponds to a batch which has been subjected to a maturing operation in an oven for twenty-four hours at 55° C. It is found in this case that the degree of dissolution is markedly lower over time and is stabilized.

EXAMPLE 5

A mixture of one hundred grams (100 g) of powder is prepared comprising:

| | |
|---|---|
| active principle: phenylpropanolamine | 12.5 g |
| active principle: chlorpheniramine | 2 g |
| hydrophobic diluting agent: | |
| dicalcium phosphate dihydrate | 70.5 g |
| lipid matrix agent: Compritol ® 888 ATO | 15 g |

In this example, the level of lipid matrix is determined in order to obtain a release profile of active principle which is similar to that of the form sold under the registered trade name Contact® of Laboratoire SmithKline Beecham.

The granules are prepared by a wet granulation process in a mixer/granulator comprising the following stages:

sieving the various constituents, mixing the active principle and Compritol® 888 ATO for five minutes, gradual addition of 23 ml of distilled water and mixing for three minutes, predrying the granules in an oven at a temperature of 45° C. for 20 minutes, screening carried out on a screening device (1 millimetre screen), drying in an oven at a temperature of 45° C. for ten hours.

The granule obtained is mixed with dicalcium phosphate in a mixer for ten minutes. 1.6 g of magnesium stearate and 1.4 g of a mixture of silicone-treated talc similar to that in Example 1 are subsequently added to 97 g of granules thus obtained.

The compression is carried out on an alternating tabletting press.

Figure 5:
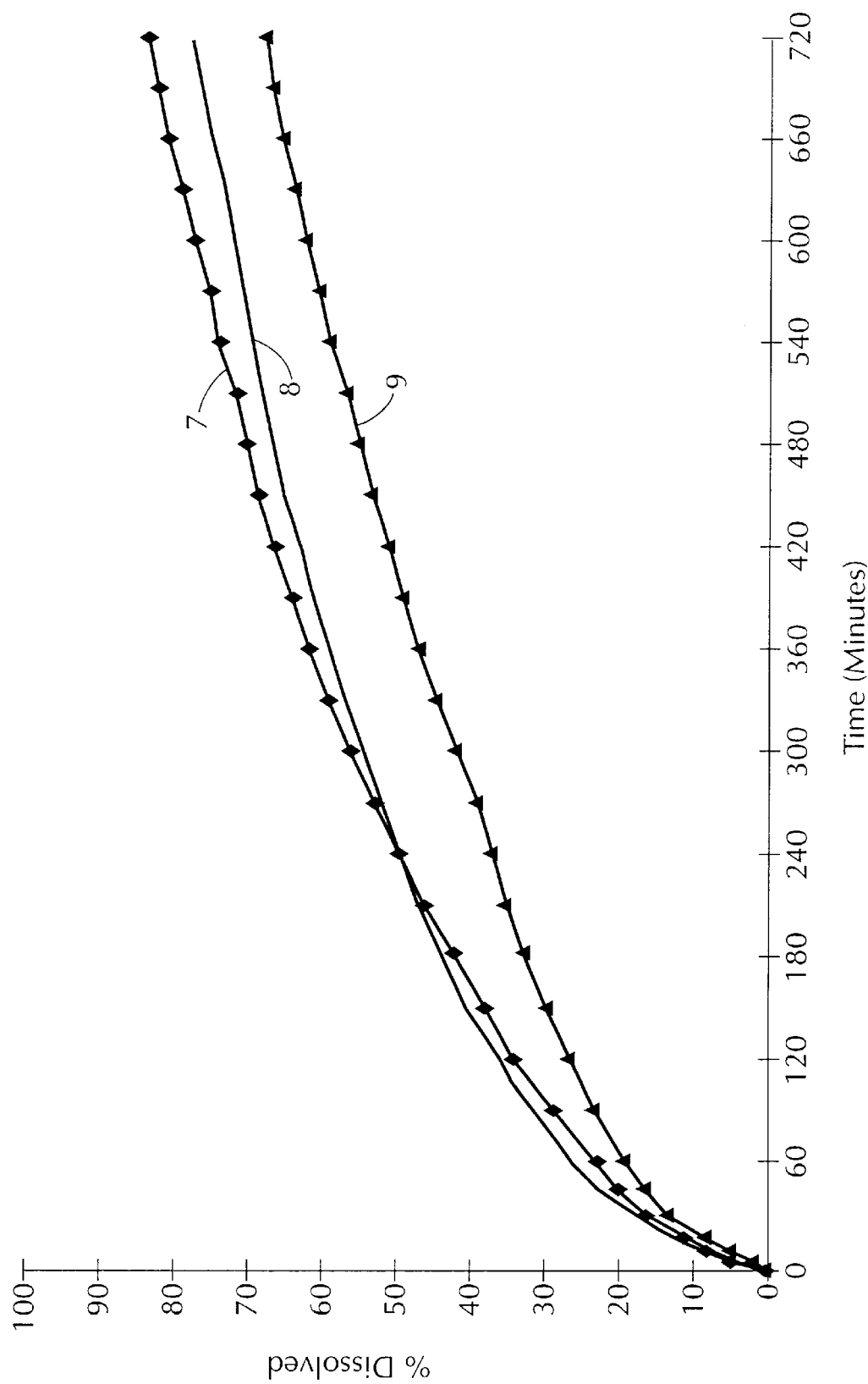
FIG. 5 is a representation as a function of the time of the dissolution profile of a batch of phenylpropanolamine and chlorpheniramine tablets which is prepared by wet granulation.

FIG. 5 is a representation of the dissolution profile of a batch of tablets, which batch is prepared according to the invention, comprising, as active principle, 75 mg of phenylpropanolamine and 12 mg of chlorpheniramine.

Curve 7 corresponds to a batch which has not been subjected to a maturing operation.

Curve 8 corresponds to a batch which has been subjected to a maturing operation in an oven for twenty-four hours at 55° C.

Curve 9 corresponds to a batch of tablets sold under the trade name Contact®.

It is found that the dissolution profile of the pharmaceutical composition prepared according to the invention corresponds to that of Contact®.

Furthermore, the form is stabilized over time by carrying out a maturing stage.

EXAMPLE 6

A mixture of 100 g of powder is prepared comprising:

| | |
|---|---|
| theophylline | 33 g |
| hydrophobic diluting agent: | |
| dicalcium phosphate dihydrate | 49 g |
| binding agent: polyvinylpyrrolidone | 3 g |
| lipid matrix agent: Compritol ® 888 ATO | 15 g |

The level of lipid matrix is determined in order to obtain a release profile of 90% of active principle over 12 hours.

The granules are prepared by a wet granulation process in a mixer/granulator comprising the following stages:

sieving the various constituents;

mixing the active principle and the adjuvants for 5 min;

gradual addition of 60 ml of water and mixing for 4 minutes;

predrying the granules in an oven at a temperature of 60° C. for 15 min;

screening carried out on a screening device (1.25 mm screen)

drying in an oven at a temperature of 40° C. for 3 hours.

The granules thus obtained are subsequently mixed with 2 g of magnesium stearate and then compressed in a rotary tabletting press.

Figure 6:
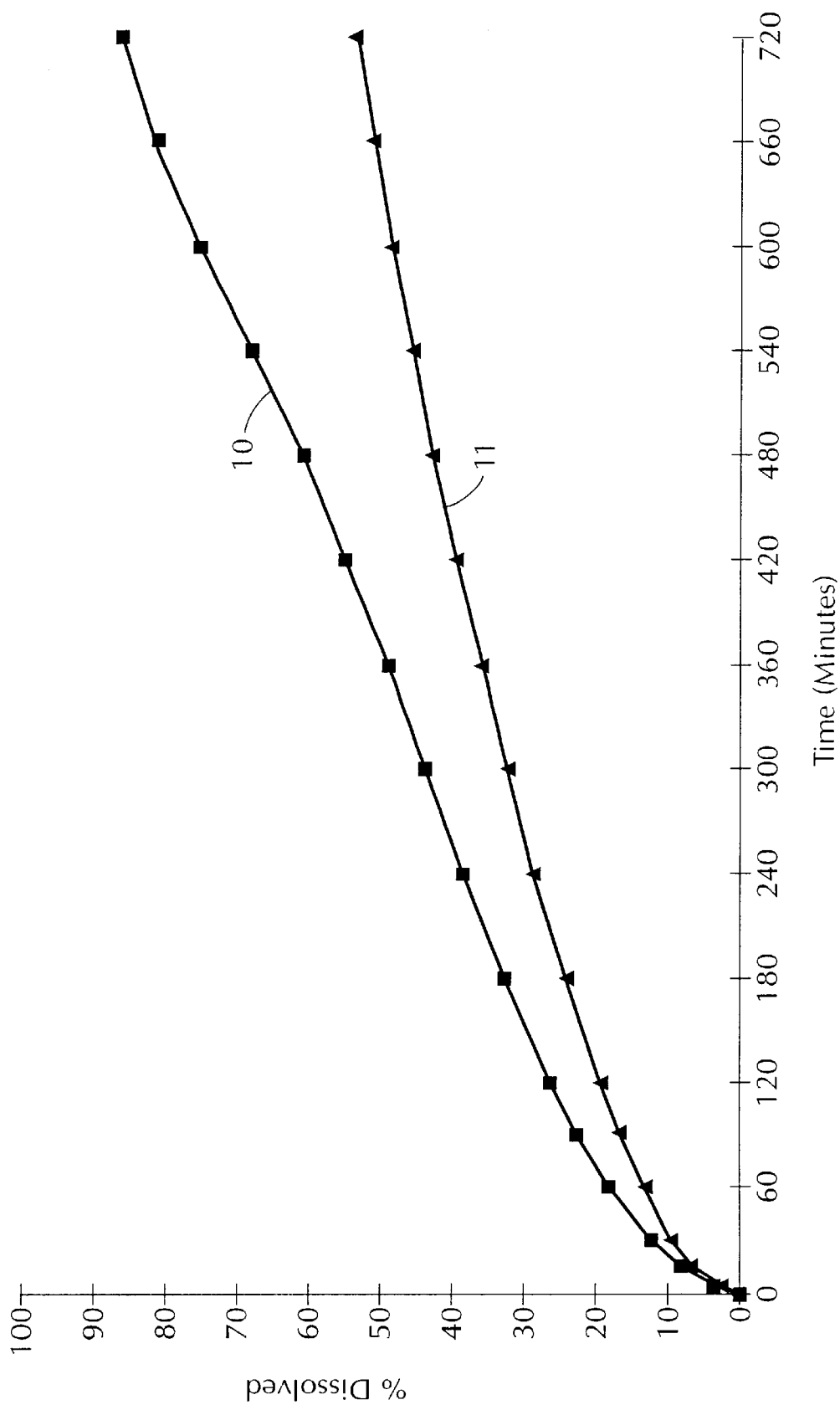
FIG. 6 is a representation as a function of the time of the dissolution profile of a batch of theophylline tablets which is prepared by wet granulation.

FIG. 6 is a representation of the dissolution profile of a batch of tablets, which is prepared according to the invention, comprising, as active principle, 100 mg of theophylline.

Curve 10 corresponds to a batch which has not been subjected to a maturing operation.

Curve 11 corresponds to a batch which has been subjected to a maturing operation in an oven for twenty-four hours at 55° C.

The process for manufacturing the composition of the invention therefore exhibits numerous advantages.

This is because this process is characterized by the low number of constituents which it employs and the low proportions of each of them.

Furthermore, it makes it possible to modulate the release profile of active principle by varying the spraying air pressure and lipid matrix agent spraying rate conditions throughout the coating stage, thus making it possible to promote the formation of a homogeneous film around the grains and/or the agglomeration of the grains.

The result is a significant saving in the production cost of modified-release pharmaceutical compositions.

What is claimed is:

1. A pharmaceutical composition with modified release comprising at least one active principle, optionally at least one adjuvant, and a lipid matrix agent comprised of partial esters of alcohol with at least one fatty acid in an amount of from about 1 percent to about 15 percent, by weight, of the total pharmaceutical composition wherein the pharmaceutical composition is obtained by a) mixing a powder comprised of an active principle and, optionally, an adjuvant, while heating and fluidizing, in order to obtain individual grains;

b) separately liquefying a lipid matrix agent comprised of partial esters of alcohol with at least one fatty-acid under warm conditions;

c) then coating the powder under warm conditions by spraying from 1 to 15% by weight of the final composition of the liquefied lipid matrix agent over the individual grains, wherein the spraying air pressure, and optionally the spraying rate, are varied throughout the coating operation so as to promote either the formation of a homogeneous film around the individual grains or the agglomeration of the individual grains with one another;

d) finally, decreasing the temperature of the combined product in order to allow the lipid matrix agent to solidify around the grains.

2. The pharmaceutical composition of claim 1, wherein the lipid matrix agent comprises either an ester of behenic acid and alcohol or an ester of palmitic/stearic acid and alcohol.

3. The pharmaceutical composition of claim 1, wherein the alcohol of the partial esters of alcohol is selected from the group consisting of glycerol, polyglycerol, propylene glycol, propylene glycol in combination with ethylene oxide, polyethylene glycol and combinations thereof.

4. The pharmaceutical composition of claim 1, wherein the active principle is selected from the group consisting of theophylline, acetyl-salicylic acid, paracetamol, ibuprofen, phenylpropanol amine, chlorpheniramine and combinations thereof.

* * * * *